(12) United States Patent
Larson

(10) Patent No.: US 7,585,309 B2
(45) Date of Patent: Sep. 8, 2009

(54) AORTIC FILTER

(75) Inventor: Christopher R. Larson, St. Paul, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 996 days.

(21) Appl. No.: 10/146,982

(22) Filed: May 16, 2002

(65) Prior Publication Data

US 2003/0216774 A1    Nov. 20, 2003

(51) Int. Cl.
*A61M 29/00* (2006.01)
(52) U.S. Cl. ...................................... 606/200
(58) Field of Classification Search ........................ None
See application file for complete search history.

(56) References Cited

U.S. PATENT DOCUMENTS

| | | |
|---|---|---|
| 3,472,230 A | 10/1969 | Fogarty |
| 3,952,747 A | 4/1976 | Kimmell, Jr. |
| 3,996,938 A | 12/1976 | Clark, III |
| 4,046,150 A | 9/1977 | Schwartz et al. |
| 4,425,908 A | 1/1984 | Simon |
| 4,590,938 A | 5/1986 | Segura et al. |
| 4,619,246 A | 10/1986 | Molgaard-Nielsen et al. |
| 4,650,466 A | 3/1987 | Luther |
| 4,706,671 A | 11/1987 | Weinrib |
| 4,723,549 A | 2/1988 | Wholey et al. |
| 4,790,812 A | 12/1988 | Hawkins, Jr. et al. |
| 4,790,813 A | 12/1988 | Kensey |
| 4,794,928 A | 1/1989 | Kletschka |
| 4,807,626 A | 2/1989 | McGirr |
| 4,873,978 A | 10/1989 | Ginsburg |
| 4,921,478 A | 5/1990 | Solano et al. |
| 4,921,484 A | 5/1990 | Hillstead |
| 4,926,858 A | 5/1990 | Giffort, III et al. |
| 4,969,891 A | 11/1990 | Gewertz |
| 4,998,539 A | 3/1991 | Delsanti |
| 5,002,560 A | 3/1991 | Machold et al. |
| 5,011,488 A | 4/1991 | Ginsburg |
| 5,053,008 A | 10/1991 | Bajaj |
| 5,071,407 A | 12/1991 | Termin et al. |
| 5,100,423 A | 3/1992 | Fearnot |
| 5,102,415 A | 4/1992 | Guenther et al. |

(Continued)

FOREIGN PATENT DOCUMENTS

DE    28 21 048    7/1980

(Continued)

OTHER PUBLICATIONS

"Atherosclerotic Disease of the Aortic Arch as a Risk Factor of Recurrent Ischemic Stroke," The New England Journal of Medicine, pp. 1216-1221 (May 1996).

(Continued)

*Primary Examiner*—Anhtuan T Nguyen
*Assistant Examiner*—Tuan V Nguyen
(74) *Attorney, Agent, or Firm*—Crompton, Seager & Tufte LLC

(57) ABSTRACT

Devices and methods for filtering embolic debris from a body lumen. The present invention includes a filter coupled to an elongate shaft. In some embodiments, the shaft may be tubular so as to be capable of allowing a guiding, therapeutic, or diagnostic device to pass therethrough.

11 Claims, 4 Drawing Sheets

U.S. PATENT DOCUMENTS

| | | | |
|---|---|---|---|
| 5,133,733 A | 7/1992 | Rasmussen et al. | |
| 5,152,771 A | 10/1992 | Sabbaghian et al. | |
| 5,152,777 A | 10/1992 | Goldberg et al. | |
| 5,160,342 A | 11/1992 | Reger et al. | |
| 5,224,953 A | 7/1993 | Morgentaler | |
| 5,329,942 A | 7/1994 | Gunther et al. | |
| 5,330,484 A | 7/1994 | Gunther | |
| 5,354,310 A | 10/1994 | Garnie et al. | |
| 5,376,100 A | 12/1994 | Lefebvre | |
| 5,421,832 A | 6/1995 | Lefebvre | |
| 5,423,742 A | 6/1995 | Theron | |
| 5,449,372 A | 9/1995 | Schmaltz et al. | |
| 4,842,579 A | 10/1995 | Shiber | |
| 5,456,667 A | 10/1995 | Ham et al. | |
| 5,462,529 A | 10/1995 | Simpson et al. | |
| 5,536,242 A | 7/1996 | Willard et al. | |
| 5,549,626 A * | 8/1996 | Miller et al. | 606/200 |
| 5,658,296 A | 8/1997 | Bates et al. | |
| 5,662,671 A | 9/1997 | Barbut et al. | |
| 5,695,519 A | 12/1997 | Summers et al. | |
| 5,720,764 A | 2/1998 | Naderlinger | |
| 5,728,066 A | 3/1998 | Daneshvar | |
| 5,749,848 A | 5/1998 | Jang et al. | |
| 5,769,816 A | 6/1998 | Barbut et al. | |
| 5,779,716 A | 7/1998 | Cano et al. | |
| 5,792,157 A | 8/1998 | Mische et al. | |
| 5,795,322 A | 8/1998 | Bouewijn | |
| 5,800,457 A | 9/1998 | Gelbfish | |
| 5,800,525 A | 9/1998 | Bachinski et al. | |
| 5,810,874 A | 9/1998 | Lefebvre | |
| 5,814,064 A | 9/1998 | Daniel et al. | |
| 5,827,324 A | 10/1998 | Cassell et al. | |
| 5,833,644 A | 11/1998 | Zadno-Azizi et al. | |
| 5,833,650 A | 11/1998 | Imran | |
| 5,846,260 A | 12/1998 | Maahs | |
| 5,848,964 A | 12/1998 | Samuels | |
| 5,876,367 A | 3/1999 | Kaganov et al. | |
| 5,895,399 A | 4/1999 | Barbut et al. | |
| 5,910,154 A | 6/1999 | Tsugita et al. | |
| 5,911,734 A | 6/1999 | Tsugita et al. | |
| 5,925,016 A | 7/1999 | Chornenky et al. | |
| 5,925,060 A | 7/1999 | Forber | |
| 5,925,062 A | 7/1999 | Purdy | |
| 5,935,139 A | 8/1999 | Bates | |
| 5,941,869 A | 8/1999 | Patterson et al. | |
| 5,941,896 A * | 8/1999 | Kerr | 606/200 |
| 5,947,995 A | 9/1999 | Samuels | |
| 5,954,745 A | 9/1999 | Gertler et al. | |
| 5,980,555 A | 11/1999 | Barbut et al. | |
| 5,989,281 A | 11/1999 | Barbut et al. | |
| 5,993,469 A | 11/1999 | McKenzie et al. | |
| 5,997,557 A | 12/1999 | Barbut et al. | |
| 6,001,118 A | 12/1999 | Daniel et al. | |
| 6,007,557 A | 12/1999 | Ambrisco et al. | |
| 6,010,522 A | 1/2000 | Barbut et al. | |
| 6,013,085 A | 1/2000 | Howard | |
| 6,027,520 A | 2/2000 | Tsugita et al. | |
| 6,042,598 A | 3/2000 | Tsugita et al. | |
| 6,051,014 A | 4/2000 | Jang | |
| 6,051,015 A | 4/2000 | Maahs | |
| 6,053,932 A | 4/2000 | Daniel et al. | |
| 6,059,814 A | 5/2000 | Ladd | |
| 6,066,149 A | 5/2000 | Samson et al. | |
| 6,066,158 A | 5/2000 | Engelson et al. | |
| 6,068,645 A | 5/2000 | Tu | |
| 6,086,605 A | 7/2000 | Barbut et al. | |
| 6,117,154 A | 9/2000 | Barbut et al. | |
| 6,129,739 A | 10/2000 | Khosravi | |
| 6,136,016 A | 10/2000 | Barbut et al. | |
| 6,142,987 A | 11/2000 | Tsugita | |
| 6,152,946 A | 11/2000 | Broome et al. | |
| 6,165,200 A | 12/2000 | Tsugita et al. | |
| 6,168,579 B1 | 1/2001 | Tsugita | |
| 6,171,327 B1 | 1/2001 | Daniel et al. | |
| 6,171,328 B1 | 1/2001 | Addis | |
| 6,179,851 B1 | 1/2001 | Barbut et al. | |
| 6,179,859 B1 | 1/2001 | Bates et al. | |
| 6,179,861 B1 | 1/2001 | Khosravi et al. | |
| 6,203,561 B1 | 3/2001 | Ramee et al. | |
| 6,206,868 B1 | 3/2001 | Parodi | |
| 6,214,026 B1 | 4/2001 | Lepak et al. | |
| 6,221,006 B1 | 4/2001 | Dubrul et al. | |
| 6,224,620 B1 | 5/2001 | Maahs | |
| 6,231,544 B1 | 5/2001 | Tsugita et al. | |
| 6,235,044 B1 | 5/2001 | Root et al. | |
| 6,235,045 B1 | 5/2001 | Barbut et al. | |
| 6,238,412 B1 | 5/2001 | Dubrul et al. | |
| 6,245,087 B1 | 6/2001 | Addis | |
| 6,245,088 B1 | 6/2001 | Lowery | |
| 6,245,089 B1 | 6/2001 | Daniel et al. | |
| 6,258,115 B1 | 7/2001 | Dubrul | |
| 6,264,663 B1 | 7/2001 | Cano | |
| 6,264,672 B1 | 7/2001 | Fisher | |
| 6,270,513 B1 | 8/2001 | Tsugita et al. | |
| 6,277,138 B1 | 8/2001 | Levinson et al. | |
| 6,277,139 B1 | 8/2001 | Levinson et al. | |
| 6,280,413 B1 | 8/2001 | Clark et al. | |
| 6,287,321 B1 | 9/2001 | Jang | |
| 6,290,710 B1 | 9/2001 | Cryer et al. | |
| 6,309,399 B1 | 10/2001 | Barbut et al. | |
| 6,319,268 B1 | 11/2001 | Ambrisco et al. | |
| 6,344,049 B1 | 2/2002 | Levinson et al. | |
| 6,361,545 B1 | 3/2002 | Macoviak et al. | |
| 2004/0167567 A1 * | 8/2004 | Cano et al. | 606/200 |

FOREIGN PATENT DOCUMENTS

| | | |
|---|---|---|
| DE | 34 17 738 | 11/1985 |
| DE | 40 30 998 A1 | 10/1990 |
| DE | 199 16 162 | 10/2000 |
| EP | 0 200 688 | 11/1986 |
| EP | 0 293 605 A1 | 12/1988 |
| EP | WO 88/09683 | 12/1988 |
| EP | 0 411 118 A1 | 2/1991 |
| EP | 0 427 429 A2 | 5/1991 |
| EP | 0 437 121 B1 | 7/1991 |
| EP | 0 472 334 A1 | 2/1992 |
| EP | 0 472 368 A2 | 2/1992 |
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| EP | 1 127 556 A2 | 8/2001 |
| FR | 2 580 504 | 10/1986 |
| FR | 2 643 250 A1 | 8/1990 |
| FR | 2 666 980 | 3/1992 |
| FR | 2 694 687 | 8/1992 |
| FR | 2 768 326 A1 | 3/1999 |
| GB | 2 020 557 B | 1/1983 |
| JP | 8-187294 A | 7/1996 |
| SU | 764684 | 9/1980 |
| WO | WO 92/03097 | 3/1992 |
| WO | WO 94/14389 | 7/1994 |
| WO | WO 94/24946 | 11/1994 |
| WO | WO 96/01591 | 1/1996 |
| WO | WO 96/10375 | 4/1996 |
| WO | WO 96/19941 | 7/1996 |
| WO | WO 96/23441 | 8/1996 |

| | | |
|---|---|---|
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | EP 0 934 729 | 8/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07521 | 2/2000 |
| WO | WO 00/07655 | 2/2000 |
| WO | WO 00/09054 | 2/2000 |
| WO | WO 00/16705 | 3/2000 |
| WO | WO 00/49970 | 8/2000 |
| WO | WO 00/53120 | 9/2000 |
| WO | WO 00/67664 | 11/2000 |
| WO | WO 00/67665 | 11/2000 |
| WO | WO 00/67666 | 11/2000 |
| WO | WO 00/67668 | 11/2000 |
| WO | WO 00/67669 | 11/2000 |
| WO | WO 01/05462 | 1/2001 |
| WO | WO 01/08595 | 2/2001 |
| WO | WO 01/08596 | 2/2001 |
| WO | WO 01/08742 | 2/2001 |
| WO | WO 01/08743 | 2/2001 |
| WO | WO 01/10320 | 2/2001 |
| WO | WO 01/15629 | 3/2001 |
| WO | WO 01/21077 | 3/2001 |
| WO | WO 01/21100 | 3/2001 |
| WO | WO 01/26726 | 4/2001 |
| WO | WO 01/35857 | 5/2001 |
| WO | WO 01/43662 | 6/2001 |
| WO | WO 01/47579 | 7/2001 |
| WO | WO 01/49208 | 7/2001 |
| WO | WO 01/49209 | 7/2001 |
| WO | WO 01/49215 | 7/2001 |
| WO | WO 01/49355 | 7/2001 |
| WO | WO 01/52768 | 7/2001 |
| WO | WO 01/58382 | 8/2001 |
| WO | WO 01/60442 | 8/2001 |
| WO | WO 01/67989 | 9/2001 |
| WO | WO 01/70326 | 9/2001 |
| WO | WO 01/72205 | 10/2001 |
| WO | WO 01/87183 | 11/2001 |
| WO | WO 01/89413 | 11/2001 |
| WO | WO 01/91824 | 12/2001 |

OTHER PUBLICATIONS

"Endovascular Grafts, Stents Drive Interventional Radiology Growth," *Cardiovascular Device Update*, 2(3):1-12 (Mar. 1996).
"Protruding Atheromas in the Thoracic Aortic and Systemic Embolization," pp. 423-427 American College of Physicians (1991).
"Recognition and Embolic Potential of Intraaortic Atherosclerotic Debris," American College of Cardiology (Jan. 1991).
Cragg, Andrew et al., "A New Percutaneous Vena Cava Filger," *AJR*, 141:601-604 (Sep. 1983).
Cragg, Andrew et al., "Nonsurgical Placement of Arterial Endoprosthesis: A New Technique Using Nitinol Wire," *AJR*, pp. 261-263 (Apr. 1983).
Diethrich et al., "Percutaneous Techniques for Endoluminal Carotid Interventions," *J. Endovasc. Surg.*, 3:182-202 (1996).
Fadali, A. Moneim, "A filtering device for the prevention of particulate embolization during the course of cardiac surgery," Surgery, 64(3):634-639 (Sep. 1968).
Haissaguerre et al., "Spontaneous Initiation of Atrial Fibrillation by Ectopic Beats Originating in the Pulmonary Veins," *The New England Journal of Medicine*, 339(10):659-666 (Sep. 1988).
Jordan, Jr. et al., "Microemboli Detected by Transcranial Doppler Monitoring . . . ," Cardiovascular Surgery, 7(1)33-38 (Jan. 1999).
Lesh, "Can Catheter Ablation Cure Atrial Fibrillation?" *ACC Current Journal Review*, pp. 38-40 (Sep./Oct. 1997).
Lund et al., "Long-Term Patentcy of Ductus Arteriosus After Balloon Dilation: an Experimental Study," Laboratory Investigation, 69(4):772-774 (Apr. 1984).
Marache et al., "Percutaneous Transluminal Venous Angioplasty . . . ," *American Heart Journal*, 125(2 Pt 1):362-366 (Feb. 1993).
Mazur et al., "Directional Atherectomy with the Omnicath™: A Unique New Catheter System," Catheterization and Cardiovascular Diagnosis, 31:17-84 (1994).
Moussa, MD, Issaam "Stents Don't Require Systemic Anticoagulation . . . But the Technique (and Results) Must be Optimal," Journal of Invasive Cardiol., 8(E):3E-7E, (1996).
Nakanishi et al., "Catheter Intervention to Venous System Using Expandable Metallic Stents," Rinsho Kyobu Geka, 14(2):English Abstract Only (Apr. 1994).
Onal et al., "Primary Stenting for Complex Atherosclerotic Plaques in Aortic and Iliac Stenoses," Cardiovascular & Interventional Radiology, 21(5):386-392 (1998).
Theron et al., "New Triple Coaxial Catheter System for Carotid Angioplasty with Cerebral Protection," American Journal of Neuroradiology, 11:869-874 (1990).
Tunick et al., "Protruding atherosclerotic plaque in the aortic archo f patients with systemic embolization: A new finding seen by transesophageal echocardiography," *American Heart Journal* 120(3):658-660 (Sep. 1990).
Waksman et al., "Distal Embolization is Common After Directional Atherectomy . . . ," American Heart Journal, 129(3):430-435 (1995).
Wholey, Mark H. et al., PTA and Stents in the Treatment of Extracranial Circulation, *The Journal of Invasive Cardiology*, 8(E):25E-30E (1996).

\* cited by examiner

AORTIC FILTER

BACKGROUND OF THE INVENTION

1. Field of the Invention

The present invention pertains to intravascular filtering devices. More particularly, the present invention pertains to devices for filtering embolic debris generated during a medical procedure.

2. Description of the Related Art

Heart and vascular disease are majors problem in the United States and throughout the world. Conditions such as atherosclerosis result in blood vessels becoming blocked or narrowed. This blockage can result in lack of oxygenation of the heart, or other vital organ which has significant consequences since the heart muscle must be well oxygenated in order to maintain its blood pumping action.

Occluded, stenotic, or narrowed blood vessels may be treated with a number of relatively non-invasive medical procedures including percutaneous transluminal angioplasty (PTA), percutaneous transluminal coronary angioplasty (PTCA), and atherectomy. Angioplasty techniques typically involve the use of a balloon catheter. The balloon catheter is advanced over a guidewire such that the balloon is positioned adjacent a stenotic lesion. The balloon is then inflated and the restriction of the vessel is opened. During an atherectomy procedure, the stenotic lesion may be mechanically cut away from the blood vessel wall using an atherectomy catheter.

During angioplasty and atherectomy procedures, embolic debris can be separated from the wall of the blood vessel. If this debris enters the circulatory system, it could block other vascular regions including the neural and pulmonary vasculature, both of which are highly undesirable. During angioplasty procedures, stenotic debris may also break loose due to manipulation of the blood vessel. Because of this debris, a number of devices, termed embolic protection devices, have been developed to filter out this debris.

Embolic debris can also be generated when performing an intravascular procedure at a location away from the heart. For example, engaging or treating the renal artery may generate embolic debris. Because of the potential dangers of embolic debris obstructing blood vessels and/or capillaries, it is important to consider capturing and/or removing debris at all areas of the vasculature.

BRIEF SUMMARY OF THE INVENTION

The present invention incorporates design and manufacturing refinements to embolic protection devices. In some embodiments, a filter can be coupled to a tubular shaft. The tubular shaft can serve dual purposes: to provides means for filtering a blood vessel and for providing means for guiding a therapeutic, ancillary or diagnostic device to an appropriate target site.

DETAILED DESCRIPTION OF THE INVENTION

Figure 1:
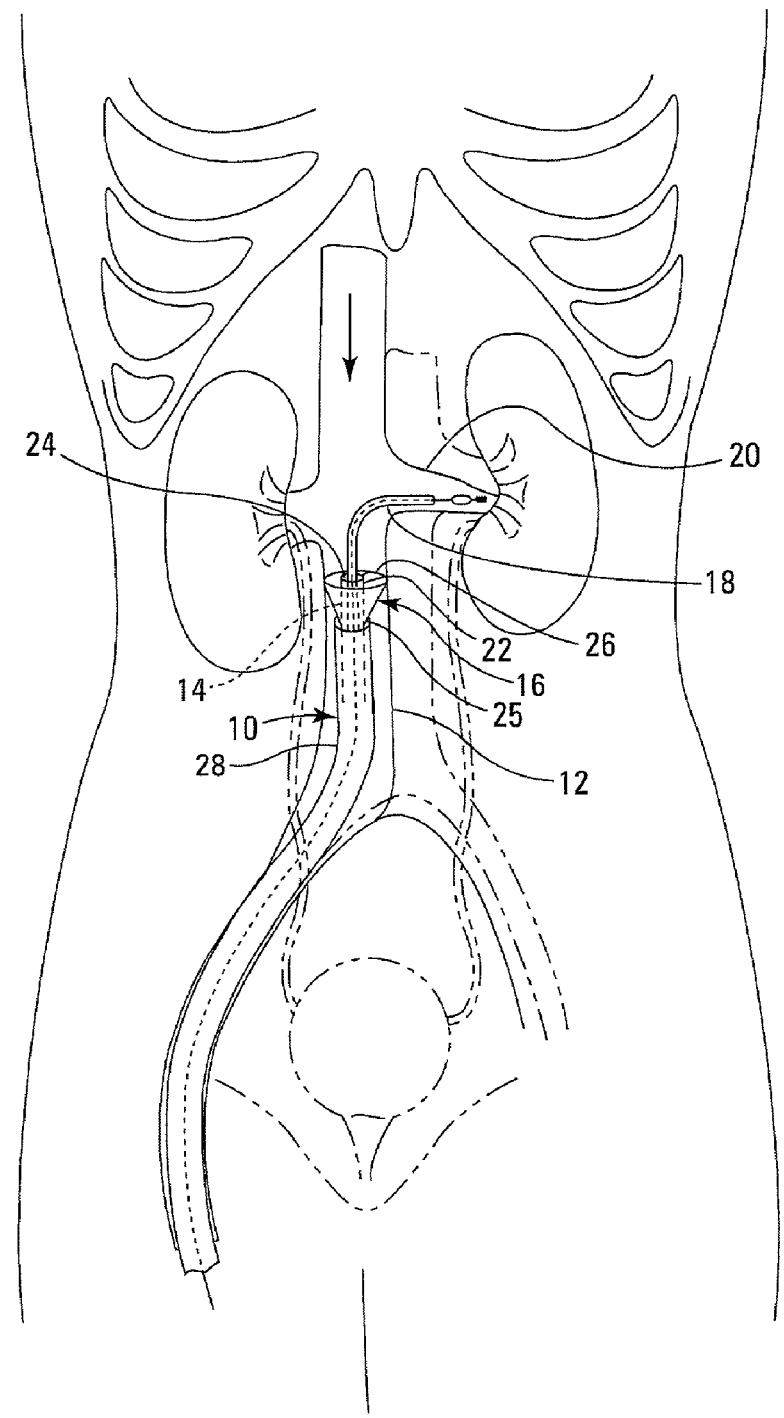
FIG. 1 is a plan overview of an embolic protection device disposed within the aorta of a patient.

The following description should be read with reference to the drawings wherein like reference numerals indicate like elements throughout the several views. The detailed description and drawings illustrate example embodiments of the claimed invention.

Intravascular medical procedures such as angioplasty or atherectomy can generate embolic debris, which might obstruct vascular regions and cause tissue damage. In addition, general navigation of medical devices through the vasculature can also generate embolic debris, for example, due to contact of the devices with vascular walls. For example, advancing a medical device to engage the renal artery for an intervention (via the femoral artery and abdominal aorta) can cause embolic debris to become dislodged and, possibly, cause complications in the lower extremities.

FIG. 1 is a plan overview of an embolic protection device 10 disposed within the aorta 12 of a patient. Embolic protection device 10 generally comprises an elongate shaft 14 having a filter 16 coupled thereto. In some embodiments, shaft 14 is tubular and allows a second medical device 18 (e.g., a diagnostic, therapeutic, or guide catheter) to be disposed therein. Embolic debris (including plaque and other debris as known to those in the art) may be generated when trying to engage, for example, the renal artery 20 with device 18. This debris may travel proximally (antegrade) in the bloodstream to the lower extremities, where it can cause tissue damage. Embolic protection device 10 can be used to filter embolic debris generated during use of device 18 or other similar devices. Moreover, device 10 may also be used during other intravascular interventions. For example, device 10 may be used to place iliac stents or to place stents elsewhere within the vasculature when a retrograde approach is used.

Shaft 14 may be comprised of a polymer, metal, metal-polymer composite, or any other suitable materials. Shaft 14 may be solid in cross-section, tubular, and/or comprise a catheter (e.g., a diagnostic, therapeutic, introducer sheath, or guide catheter). For example, shaft 14 may be generally constructed according to techniques used to construct typical guide catheters. Shaft 14 includes a proximal end (not shown), a distal end 22, and a lumen 24 extending therethrough.

Filter 16 may be disposed near distal end 22. Filter 16 may be comprised of a polyurethane sheet and include at least one opening that may be, for example, formed by laser cutting. The holes or openings are sized to allow blood flow therethrough but restrict flow of debris or emboli floating in the body lumen or cavity.

Filter 16 may be, but not limited to, a generally cone-shape, and have a proximal end 25 and a distal end 26. Proximal end 25 may be a narrow, "V"-shaped end and can be fixedly secured or formed to shaft 14. Distal end 26 has a relatively wide opening. Filter 16 operates between a first generally collapsed configuration and a second generally expanded configuration for collecting debris in a body lumen. Filter 16 may include a frame that is comprised of a self-expanding metal alloy (e.g., nickel-titanium alloy). According to this embodiment, filter 16 may be biased to be in the second (expanded) configuration.

Device 10 may include an outer sheath 28 disposed over at least a portion of shaft 14. Sheath 28 may be a delivery sheath used during delivery of device 10 to the vasculature. To use sheath 28 as a delivery sheath, shaft 14 is disposed within sheath 28 so that filter 16 is at least partially collapsed therein. In some embodiments, a portion of filter 16 may extend distally from a distal end of sheath 28 as described below and shown in FIG. 6. With filter 16 collapsed within sheath 28, device 10 can be advanced through the vasculature to a desired location. Once at the desired location, sheath 28 can be retracted proximally relative to shaft 14, allowing filter 16 to shift to the second (expanded) configuration.

Figure 2:
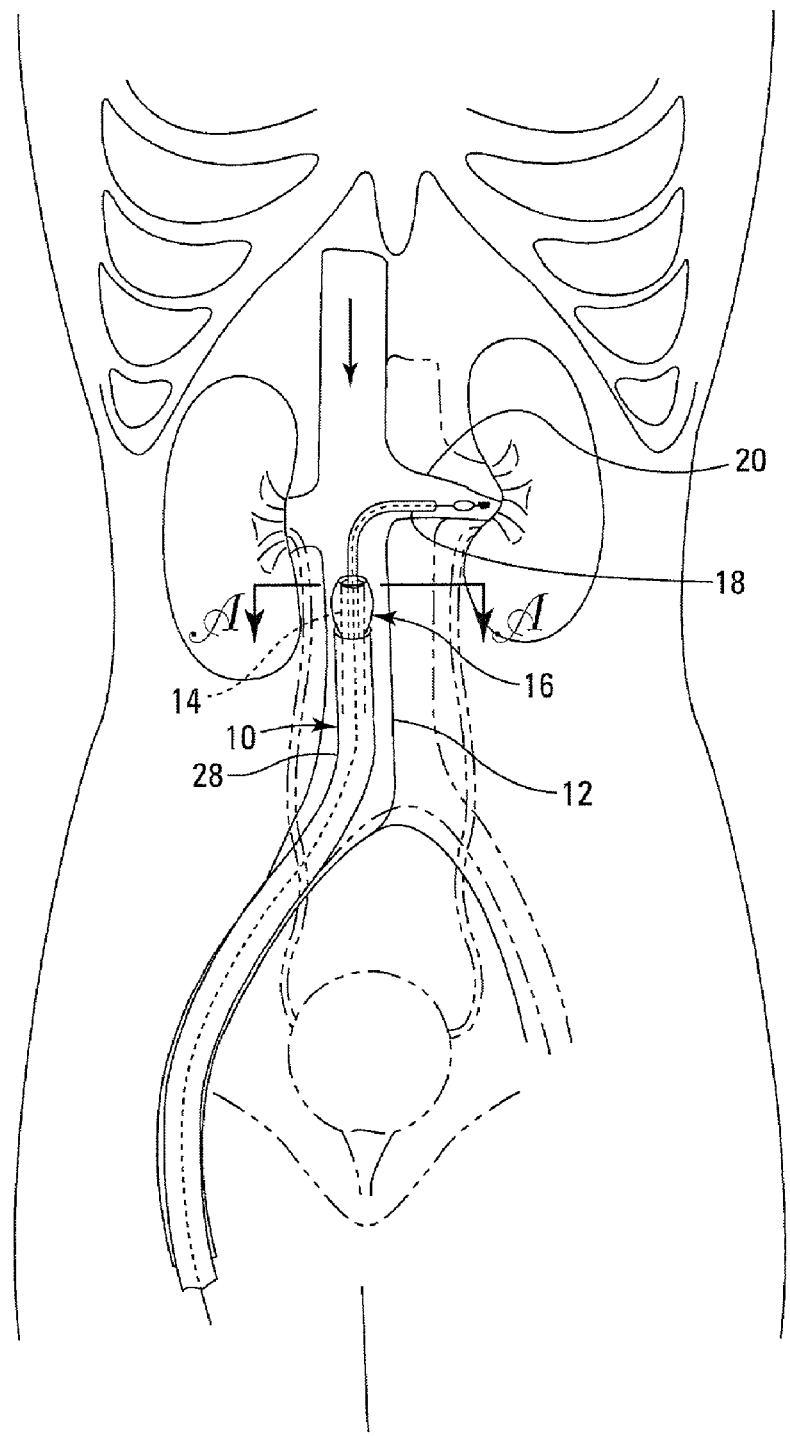
FIG. 2 is a plan overview of an embodiment of an embolic protection device where the filter is partially collapsed and configured for removal from the vasculature of the patient.

FIG. 2 is a plan overview of an embodiment of embolic protection device 10 where filter 16 is partially collapsed and configured for removal from the vasculature of the patient. A number of different structures and methods can be utilized to remove device 10. For example, sheath 28 can be advanced distally over filter 16, collapsing filter 16 and encapsulating it within sheath 28. Once encapsulated within sheath 28, filter 16 (and device 10) can be removed by withdrawing proximally through the vasculature. Alternatively, a pull cord or other device may be coupled to filter 16. Some of these embodiments are illustrated in sections taken through line A-A in FIGS. 3-4.

Figure 3:
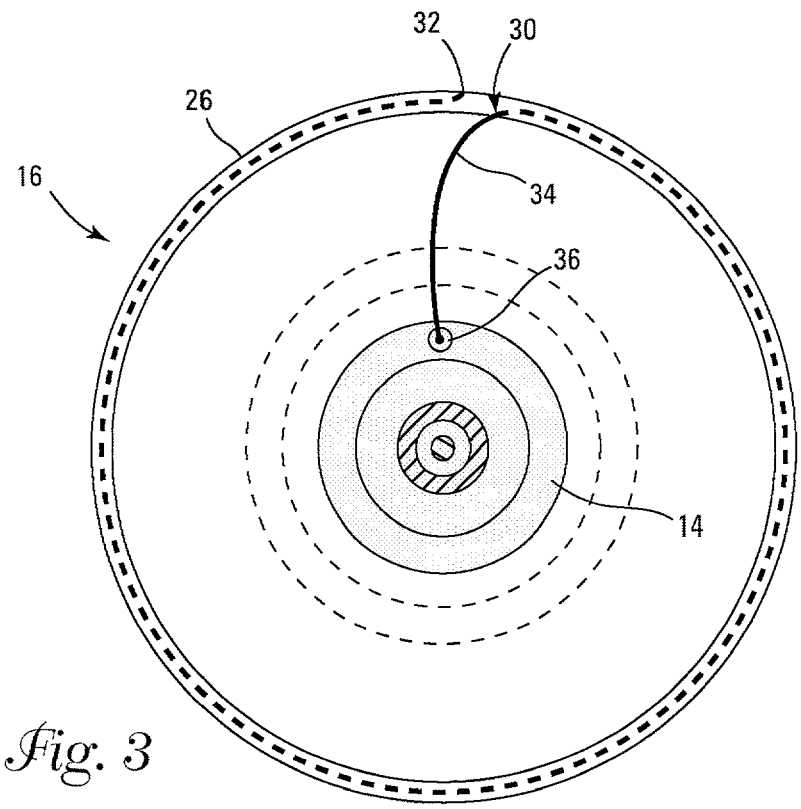
FIG. 3 is a top view of the embolic protection device illustrating the filter and a pull cord for collapsing the filter.

FIG. 3 is a top view of embolic protection device 10 showing filter 16 and a pull cord 30 for collapsing filter 16. Pull cord 30 may be disposed at or otherwise coupled to distal end 26 of filter 16. As shown, pull cord 30 is threaded through a portion of distal end 26 in a manner analogous to a stitch. A distal end 32 of pull cord 30 may be generally fixed to a portion of distal end 26. Moreover, the individual stitches of pull cord 30 through distal end 32 are configured so that pull cord 30 can be tightened to collapse or otherwise decrease the circumference of filter 16 (as shown in FIG. 2).

Pull cord 30 has at least one loop portion 34 that extends between distal end 26 of filter 16 and shaft 14. In some embodiments, shaft 14 includes a cord lumen 36 extending along the longitudinal axis of shaft 14. According to this embodiment, pull cord 30 may be passed through lumen 36 and extend proximally to a convenient location for a clinician to actuate or "pull" pull cord 30. It can be appreciated that the precise location of cord lumen 36 within shaft 14 may be altered without departing from the spirit of the invention. For example, cord lumen 36 may be disposed more closely to the outer surface of shaft 14 than the inner surface. This later configuration may be described as being asymmetrically disposed.

To collapse filter 16 with pull cord 30, the clinician actuates or pulls pull cord 30 in the proximal direction. When pulled, pull cord 30 tightens within distal end 26 and tends to decrease the circumference of filter 16. Once partially collapsed, sheath 28 may be advanced over filter 16 so that device 10 can be removed from the vasculature.

The embodiment shown in FIG. 3 allows the clinician to minimize the release of captured embolic debris from filter 16 when collapsing filter 16. Using pull cord 30 to collapse filter 16 allows the clinician to apply force to collapse filter 16 essentially at distal end 26 to contain debris within filter 16 during retrieval.

Pull cord 30 may be generally metallic or be comprised of any suitable material including polymers. In some embodiments, pull cord 30 may include a portion that comprised of or plated with a radiopaque material. Radiopaque materials are understood to generally produce a relatively bright image on a fluoroscopy screen during a medical procedure. This relatively bright image aids the user of device 10 in determining its location. Radiopaque materials include, but are not limited to, gold, platinum, and plastic material loaded with a radiopaque filler.

Figure 4:
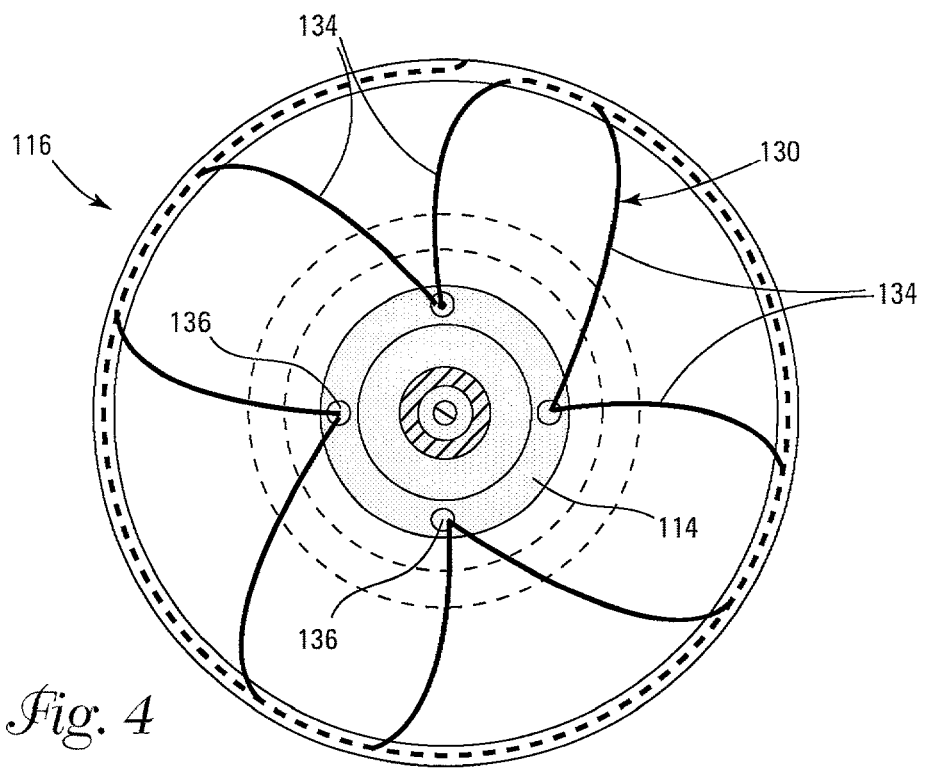
FIG. 4 is a top view of an alternative embolic protection device illustrating the filter and a plurality of pull cords for collapsing the filter.

FIG. 4 is a top view of an alternative filter 116 and pull cord 130 that are essentially the same in form and function as filter 16 and pull cord 130, except that pull cord 130 has a plurality of loops portions 134 extending between filter 116 and shaft 114. Shaft 114 is essentially the same as shaft 14, except that shaft 114 includes a plurality of cord lumens 136. Thus, pull cord 130 essentially includes a plurality of pull cords (in this case four individual regions) that can be actuated to collapse filter 16 as described above.

Figures 5, 6:
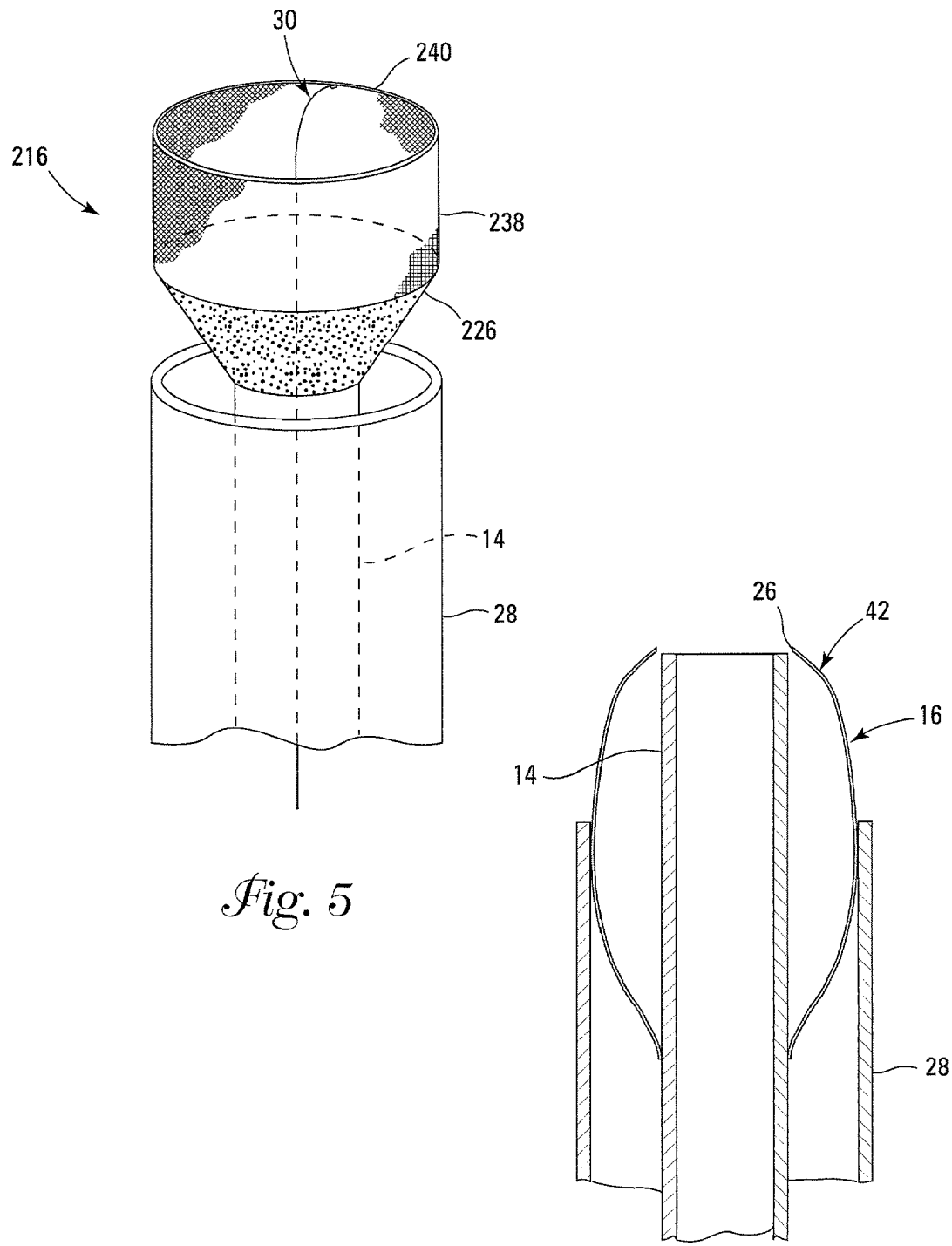
FIG. 5 is a prospective view of an alternative embodiment of a filter for use with an embolic protection device.
FIG. 6 is a partial cross-sectional view of the embolic protection device disposed in a delivery sheath in a configuration suitable for navigating the vasculature of a patient.

FIG. 5 is a prospective view of an alternate filter 216 that is essentially the same in form and function as filter 16, except that filter 216 includes a non-filtering region 238 extending distally from distal end 226. According to this embodiment, pull cords 30/130 can be coupled to a distal end 240 of non-filtering region 238 and then be used essentially as described above.

In some embodiments, non-filtering region 238 may act as an extension of filter 216 to increase the holding capacity of embolic debris within filter 216. It can be appreciated that non-filtering region 238 is constructed to be solid (i.e., non-porous) in structure and would capture or filter only a minimum amount of embolic debris. Thus, if collapsing filter 216 dislodged any embolic debris, the debris would still be contained within non-filtering region 238 so that the debris can be effectively removed from the patient.

FIG. 6 is a partial cross-sectional view of embolic protection device 10 disposed in delivery sheath 28 in a configuration suitable for navigating the vasculature of a patient. In some embodiments, sheath 28 may be configured over a portion of filter 16 so that filter 16 is collapsed and forms a tapered distal tip 42 to device 10. Tapered distal tip 42 provides device 10 with a generally atraumatic distal end.

In use, embolic protection device 10 can be advanced to a landing area within the aorta as shown in FIG. 1. Filter 16 may be expanded by advancing shaft 14 or retracting sheath 28. Medical device 18 can then be advanced to renal artery 20. Filter 16 can then be collapsed as shown in FIG. 2 and withdrawn as shown in FIG. 2. Another filter may be advanced and positioned at the landing area if desired. Alternately, medical device 18 can be removed prior to collapsing and removing filter 16.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. An embolic protection device, comprising:
an elongate tubular shaft having a proximal end, a distal end, and a lumen extending at least in part therethrough;
a filter coupled to the shaft proximate the distal end, the filter having a distal mouth region, the filter including an extension portion of non-filtering material extending at least in part distally beyond the distal mouth region; and
a plurality of pull cords coupled to the mouth portion, the pull cords forming a plurality of loop portions, and extending proximally along a longitudinal axis of the shaft such that altering the position of the pull cords shifts the filter between a first generally collapsed configuration and a second generally expanded configuration, wherein each of the loop portions includes a first end region disposed in a first cord lumen formed in a tube wall of the tubular shaft and a second end region disposed in a second cord lumen formed in the tube wall.

2. The embolic protection device of claim 1, wherein the tubular shaft include a tube wall having a plurality of cord lumens formed therein and wherein the pull cords are disposed in the cord lumens.

3. The embolic protection device of claim 1, wherein the pull cords extend through the lumens of the tubular shaft.

4. The embolic protection device of claim 1, wherein the pull cords are threaded through a portion of the filter.

5. The embolic protection device of claim 1, wherein at least one pull cord includes a metal.

6. The embolic protection device of claim 1, wherein at least one pull cord includes a radiopaque material.

7. The embolic protection device of claim 1, further comprising a delivery sheath disposed over the tubular shaft.

8. The embolic protection device of claim 1, further comprising a medical device disposed within the lumen of the tubular shaft.

9. The embolic protection device of claim 8, wherein the medical device includes a guidewire.

10. The embolic protection device of claim 1, wherein the medical device includes a catheter disposed over the guidewire.

11. The embolic protection device of claim 10, wherein the catheter includes an expandable balloon.

\* \* \* \* \*

UNITED STATES PATENT AND TRADEMARK OFFICE
CERTIFICATE OF CORRECTION

PATENT NO. : 7,585,309 B2  Page 1 of 1
APPLICATION NO. : 10/146982
DATED : September 8, 2009
INVENTOR(S) : Christopher R. Larson It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1651 days.

Signed and Sealed this

Fourteenth Day of September, 2010

David J. Kappos
*Director of the United States Patent and Trademark Office*